US006391626B1

(12) United States Patent
Adams et al.

(10) Patent No.: US 6,391,626 B1
(45) Date of Patent: May 21, 2002

(54) CULTURE MEDIUM AND DEVICE USING BALLASTED PH INDICATORS FOR DETECTION AND ENUMERATION OF MICROORGANISMS

(75) Inventors: Carl A. Adams, Apple Valley; Kurt J. Halverson, Lake Elmo; Gary E. Krejcarek, White Bear Lake, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/378,991

(22) Filed: Aug. 23, 1999

(51) Int. Cl.[7] ............... C12M 1/16; C12M 1/34; C12Q 1/04
(52) U.S. Cl. .................. 435/287.9; 435/34; 435/39; 435/288.3; 435/288.7
(58) Field of Search ............... 435/29, 30, 32, 435/39, 287.1, 287.7, 287.9, 288.3, 288.7, 305.1, 305.4

(56) References Cited

U.S. PATENT DOCUMENTS

| | | | |
|---|---|---|---|
| 3,881,993 A | * | 5/1975 | Freake et al. |
| 4,029,597 A | | 6/1977 | Neisius et al. ............... 252/408 |
| 4,029,598 A | | 6/1977 | Neisius et al. ............... 252/408 |
| 4,565,783 A | | 1/1986 | Hansen et al. ............... 435/299 |
| 4,861,709 A | | 8/1989 | Ulitzur et al. ................. 435/6 |
| 5,039,492 A | * | 8/1991 | Sasski et al. |
| 5,089,413 A | | 2/1992 | Nelson et al. ............... 435/254 |
| 5,232,838 A | | 8/1993 | Nelson et al. ................. 435/30 |
| 5,238,809 A | | 8/1993 | Wolfbeis ........................ 435/4 |
| 5,292,840 A | | 3/1994 | Heilmann et al. .......... 526/304 |
| 5,384,411 A | | 1/1995 | Robotti et al. |
| 5,498,525 A | | 3/1996 | Rees et al. .................... 435/29 |
| 5,561,097 A | | 10/1996 | Gleason et al. ............. 502/402 |
| 5,601,998 A | | 2/1997 | Mach et al. .................. 435/34 |
| 5,723,308 A | | 3/1998 | Mach et al. .................. 435/34 |
| 5,763,251 A | | 6/1998 | Gasson ........................ 435/115 |
| 5,853,669 A | * | 12/1998 | Wolfbeis |
| 5,910,447 A | * | 6/1999 | Lawrence et al. |
| 5,914,240 A | | 6/1999 | Sanders ..................... 435/7.32 |
| 5,958,675 A | | 9/1999 | Wicks et al. .................... 435/5 |
| 5,976,827 A | * | 11/1999 | Jeffrey et al. |

FOREIGN PATENT DOCUMENTS

| | | |
|---|---|---|
| DE | 196 17 338 A1 | 11/1997 |
| EP | 0 519 198 A2 | 12/1992 |
| WO | WO 93/07483 | 4/1993 |
| WO | WO 96/06183 | 2/1996 |

OTHER PUBLICATIONS

Excerpt: Mar., "Advanced Organic Chemistry," *Wiley Inter-Science*, 4th Edition, 1992, pp. 420–421.

* cited by examiner

*Primary Examiner*—William H. Beisner
(74) *Attorney, Agent, or Firm*—John A. Burtis

(57) ABSTRACT

Media, devices and methods using ballasted pH indicators to detect and enumerate bacterial colonies in a sample are described. The ballasted pH indicators limit the diffusion of the indicator or fluorescent indicator zones associated with the growing microbial colonies in the medium. In addition, the ballasting of certain typically toxic indicators may render these indicators harmless to bacteria without adversely affecting their pH indicating ability.

31 Claims, 1 Drawing Sheet

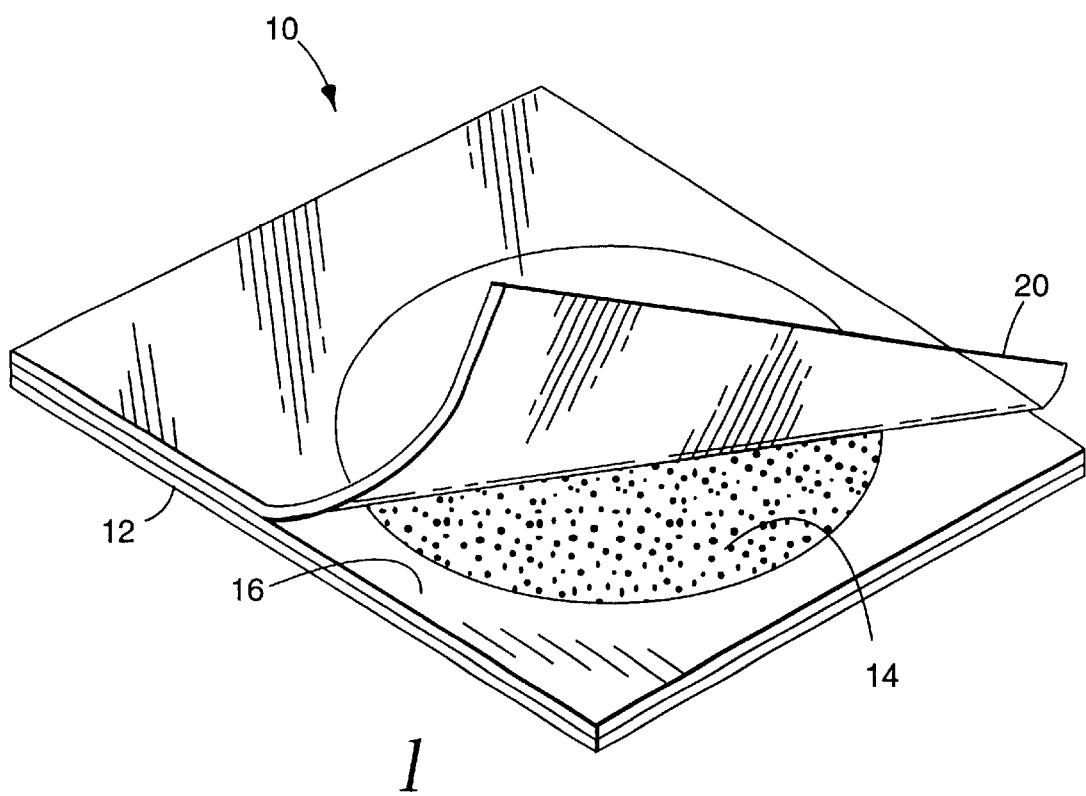

CULTURE MEDIUM AND DEVICE USING BALLASTED PH INDICATORS FOR DETECTION AND ENUMERATION OF MICROORGANISMS

FIELD

This invention relates to culture media, devices and methods for detecting and enumerating microorganisms in a sample, and particularly relates to media, devices and methods that employ ballasted pH indicators.

BACKGROUND

Methods of detecting microorganism growth using pH indicators have long been known. The presence of microorganisms is usually detected by a visual color or fluorescence change of the pH indicator in a zone surrounding the growing microbial colony that is caused by the reaction of the indicator with acid produced by the growing microorganisms.

A common problem when using pH indicators is that as the growing microorganisms continue to produce acid, the colored or fluorescent indicator zones increase in size and may begin to merge and overlap with the indicator zones of the surrounding nearby colonies. After a typical 18 to 24 hour incubation period, the adjacent indicator zones typically diffuse together, thereby making it difficult to differentiate between and enumerate the individual indicator zones which correspond to individual colonies.

The use of pH indicators at very high concentrations has recently been shown to decrease the detection time for coliform bacteria in a culture medium without deleteriously affecting bacterial growth. However, even with a decreased detection time, large numbers of colonies may prevent an observer from being able to distinguish between colonies that produce acid and those that do not produce acid, because the indicator zones may increase in size and diffuse together during incubation.

Another potential problem when selecting pH indicators is that some indicators that demonstrate good indicating and/or spectral properties are toxic to microbiological growth.

SUMMARY

There is a need in the art for media that overcomes the deficiencies of the prior art that limit the spread of indicator zones when using pH indicators. In particular, there is a need for media, devices and methods of use thereof that control the spread of indicator zones when using pH indicators.

In one aspect of the present invention, a culture medium includes a medium for growing microorganisms and at least one ballasted pH indicator. The media has growth nutrients for the targeted microorganisms or growth nutrients may be added for use. Preferably, the medium is a cold water soluble powder. A variety of pH indicators may be used in the present invention, including potentially some indicators normally toxic to microbiological growth. The indicators include monoazo dyes; polyazo dyes; amino-, hydroxy-, and aminohydroxy- arylmethanes, including di- and tri-arylmethanes; modified phenolphthaleins; modified sulfonphthaleins; anthroquinones; xanthenes; polycylic aromatics; and naphthofluoresceins. Preferred ballasts include high molecular weight substances selected from the group consisting of cellulose; modified celluloses; polyvinyl alcohol (PVA); dextrans; amino-modified dextrans; guar gums; modified guar gums; xanthan gum; locust bean gum; and other polycarbohydrate gums.

In another aspect of the present invention, a device for detection and/or enumeration of microorganisms includes a culture medium as described above. A preferred device comprises a self-supporting waterproof substrate, an optional foam spacer, and a cover.

In still another aspect of the present invention, a method of detecting and enumerating microorganisms in a sample includes the steps of adding a sample suspected of including microorganisms to a culture medium containing a ballasted pH indicator, growing the microorganisms in the presence of the culture medium, and detecting a color or fluorescence change of the ballasted pH indicator in the medium.

The present invention overcomes deficiencies of the prior art by controlling the spreading of colored or fluorescent indicator zones throughout a culture medium. Control of the colored or fluorescent indicator zones is achieved by binding the pH indicator to a ballast. Surprisingly, these ballasted pH indicators control the spreading of the indicator zones in the culture medium without affecting the acid production capability of colonies in the medium. As a result, the merging of adjacent indicator zones is reduced or eliminated and differentiation between individual indicator zones may be enhanced even after an extended incubation time.

The present invention also provides media, devices and methods that may permit the use of pH indicators which normally would be considered toxic to microbiological growth. By ballasting the pH indicators, the indicators may not exhibit toxicity to the microorganisms.

BRIEF DESCRIPTION OF THE DRAWING

The figure is an illustration of a thin film culture plate device containing the culture medium of the present invention comprising a ballasted pH indicator.

DETAILED DESCRIPTION

The present invention provides media, devices and methods that may be used to detect and enumerate microorganisms in a sample. Although a variety of products and processes may be used to detect and enumerate microorganisms in a sample, the media, devices and methods of the present invention greatly simplify such detection and enumeration of microorganisms through the use of ballasted pH indicators. The culture media, devices, and methods not only permit a rapid determination of results, but also maintain discrete indicator zones after even an extended incubation time.

In addition, the present invention may allow the use of pH indicators that possess desirable spectral and pH indicating properties but are toxic to microorganisms. Ballasting these indicators may reduce or eliminate such toxicity by preventing the indicator from entering the microorganism cell and thereby causing decreased activity or cell death.

For the purposes of this invention, "ballast" means a high molecular weight substance that chemically binds to a pH indicator, but does not substantially impair the function of the pH indicator. A "ballasted pH indicator" means a pH indicator that has a ballast chemically bound to it. To "ballast" means to bind a ballast to a pH indicator. "Indicator zone" means a typically circular region surrounding a growing microorganism colony and has a different color or fluorescence than the surrounding culture medium due to the reaction of the acid produced by the colony and a pH indicator. The more restricted the diffusion or spreading of the indicator throughout the medium, the smaller the resulting "indicator zone". The indicator zones are thus generally visually different in appearance from the remainder of the culture medium.

The present invention includes a culture medium with a ballasted pH indicator. A variety of culture media are suitable for use in the present invention. The medium will include various nutrients or have nutrients added, depending on the target microorganisms. A typical culture medium comprises a carbon source such as a carbohydrate, a nitrogen source such as amino acids or protein hydrolysates, and trace nutrients. The culture media may also include at least one gelling agent. A preferred media is a cold-water soluble powder, such as described in U.S. Pat. No. 5,232,838.

The ballasts of the present invention are preferably high molecular weight substances. These substances are capable of binding to a pH indicator. Preferably, the ballasts are hydrophilic, have high molecular weight and possess at least one reactive functional group, such as a hydroxyl, carboxyl, or amino group that chemically binds to the pH indicator. It is preferred that the molecular weight of the ballast be greater than about 5,000 and more preferred that the molecular weight is greater than about 40,000. Suitable ballasts useful in this invention include cellulose, modified celluloses, polyvinyl alcohol (PVA), dextrans, amino-modified dextrans, modified guar gums, guar guns, xanthan gums, and locust bean gums, with polyvinyl alcohol and amino-modified dextrans being preferred because of the ease of reactivity of these ballasts with pH indicators. Furthermore, ballasted pH indicators including these ballasts are relatively easy to incorporate into various media.

A variety of pH indicators may be used in the present invention. Suitable indicators will change color or change fluorescence as the acid level of the culture medium changes. As a microorganism colony grows, the colony produces acid that reacts with the pH indicator to produce an indicator zone surrounding the colony that is a different color or fluorescence than the rest of the culture medium. For example, the indicator carboxy phenol red generally produces a red-colored culture medium that changes to a yellow color as the level of acid increases. In addition to ballasted pH indicators that change color, ballasted pH indicators that change in fluorescence may also be used in the culture media, devices, and methods of the invention. In the case of such pH ballasted indicators, the indicator zones fluoresce in the presence of increased acid, whereas the culture medium not in contact with increased acid levels does not fluoresce.

Suitable pH or acid-base indicators useful in this invention include indicators commonly classified as monoazo dyes; polyazo dyes; amino-, hydroxy-, and aminohydroxy-arylmethanes (di- and tri-arylmethanes); modified phenolphthaleins and sulfonphthaleins; anthroquinones; xanthenes; polycyclic aromatics; and naphthofluoresceins. Preferred pH indicators include modified phenolphthaleins and sulfonphthaleins, naphthofluoresceins, and the monoazo dyes. Representative dyes from the listed classes include carboxy phenol red and amino phenol red (both of which are modified sulfonphthaleins); methyl red, ethyl red and 2-(2, 4-dinitrophenylazo)-6-[N-methyl-N-(2-hydroxysulfonyl-oxy-ethylsulfonyl)amido]-1-naphthol-3-sulfonic acid ("DNSA") (all of which are monoazo dyes); and carboxy-SNARF™ and carboxySNAFL™ (both of which are naphthofluoresceins). DNSA indicator can be prepared as described in U.S. Pat. No. 4,029,598 (Neisius, et al.), and carboxySNARF™ and carboxySNAFL™ are available from Molecular Probes, Eugene, Oreg. Particularly preferred dyes are carboxy phenol red, carboxy chlorophenol red, aminophenol red, aminochlorophenol red, carboxySNARFS™, carboxySNAFLS™, and DNSA. Processes are known for suitably modifying indicator dyes so that an appropriate functional group is available to subsequently covalently bind to a high molecular weight ballast. For example, published European Patent Application No. 0 519 198 A2 (Robotti) discloses a process for such a modification of various phthalein-type pH indicator dyes.

Generally, any pH indicator which changes color or fluorescence in the desired pH range for the desired microorganism and possesses one or more reactive groups that do not participate in the acid-base reaction chemistry of the indicator may be used to bind the indicator to a high molecular weight ballast. Preferably, the pH indicator covalently bonds to the ballast without substantially adversely altering the pKa of the indicator.

Particularly preferred pH indicator and ballast combinations of this invention include DNSA indicator bound to polyvinyl alcohol, and carboxy phenol red bound to an amino-modified dextran of molecular weight approximately 40,000 or higher because of ease of reaction and incorporation into the media.

Coupling agents may be used as aids in bonding the pH indicator to a ballast. For example, the coupling agents EDC [1-(3-dimethylaminopropyl)-3-ethyl carbodiimide hydrochloride] and HOBt (1-hydroxy-benzotriazole hydrate) can aid in covalently bonding the carboxyl group of carboxy phenol red to the amino group of an amino-modified dextran. The use of such coupling agents is described in "Advanced Organic Chemistry", by Jerry March, Wiley InterScience, 4th Edition, 1992, pp. 420–421.

The ballasted pH indicators of the invention restrict or limit spreading of the indicator zones through the culture medium. Controlling the spreading of indicator zones results in smaller or more discrete indicator zones that are less likely to diffuse together and thus may be more readily differentiated from one another. Less spreading of indicator zones leads to simpler and more accurate detection and enumeration of the growing microorganism colonies. Spreading of the indicator zones is particularly a problem where there are relatively high numbers of acid-producing colonies present. The ballasted pH indicators may also be useful in better distinguishing between acid-producing colonies and those that do not produce acid in a mixed sample.

The ballasted pH indicators of this invention may also be capable of reducing or eliminating the toxicity of pH indicators to a growing microorganism colony. This reduction in toxicity may be due to the inability of the ballasted pH indicator to penetrate into the microorganism cells. It is believed that the pH indicator cannot cross the cell membrane for some reason, e.g., size, charge, etc. Such ballasting of the pH indicator to the molecule may prevent the pH indicator from entering the microorganism cell and causing decreased cellular activity or cell death.

Many devices are suitable for use in the present invention. Any device that incorporates the media described above and is capable of use for detection and/or enumeration of microorganisms may be used. The figure illustrates a preferred device of the present invention. With reference to the figure, a thin film culture device is depicted. Thin film culture devices have been previously described in U.S. Pat. Nos. 4,565,783; 5,089,413; and 5,232,838.

With continuing reference to the figure, the thin film culture device 10 includes a body member having a self-supporting, substantially waterproof substrate 12. Substrate 12 is preferably a relatively stiff material made of a waterproof material such as polyester, polypropylene, or polystyrene that does not substantially absorb water. Other suitable waterproof materials include substrates such as paper containing a waterproof polyethylene coating.

A surface of substrate 12 is coated with a layer of culture medium 14 which is then dried to provide a dry medium on substrate 12. Alternatively, a layer of adhesive (not depicted)

may be coated on substrate 12 that serves to hold a culture medium that may be applied as a powder. The adhesives preferably are sufficiently transparent when hydrated to allow viewing of bacterial colonies growing on the surface of the substrate through the coated substrate. The adhesive is coated on the substrate in a thickness that allows the substrate to be substantially uniformly coated with dry culture medium without completely embedding the media in the adhesive.

If the liquid culture medium of this invention is to be used in a dry form or as a dry powder, the reagents, nutrients, gums and ballasted pH indicator are added as a liquid to the substrate and then dried. The culture medium of this invention may be readily dried by heating liquid medium in an oven at about 100° C. until essentially all of the water in the liquid has evaporated. If the medium is heated after the water has evaporated, however, the medium may begin to degrade.

An optional foam spacer 16 having an opening in the foam is adhered to the medium coated surface of substrate 12. The foam spacer which substantially covers the periphery of substrate 12 defines the area which is to be inoculated with a sample and serves to prevent the sample from the substrate. In an alternate embodiment, a device may not include a foam layer, and the amount of sample is contained on the substrate by the components of the medium alone.

A cover 20 may be attached to one edge of the upper surface of the foam spacer 16. The figure depicts a cover sheet 20 that is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene. The cover sheet is optionally coated with additional gums and a second indicator such as triphenyltetrazolium chloride (TTC).

In the methods of the present invention, sample is added to a media as set forth above. In a preferred embodiment, sample is added to a device, such as the device illustrated in the figure that includes a media of the present invention. The inoculum may be spread over the substrate 12 and a cover may be placed over substrate 12. A method of spreading the inoculum includes using a weighted tool to move along the cover and spread the inoculum. In the case of dry media, as the inoculum contacts and is spread on substrate 12, the medium hydrates to form a growth-supporting nutrient gel. The inoculated device is then incubated for a predetermined time after which the number of colonies or microorganisms growing on the substrate may be counted.

Although the use of the culture medium containing ballasted pH indicators on a thin film device is described above, those of ordinary skill in the art will recognize that the culture medium containing ballasted pH indicators may be used in other culturing devices which are known in the art. For example, the culture medium may be used as a broth and used to grow bacteria in suspension or the culture medium may be used to grow bacteria on agar plates.

EXAMPLES

The following examples are offered to aid in understanding of the present invention and are not to be construed as limiting the scope thereof. Unless otherwise indicated, all parts and percentages are by weight.

Example 1

Preparation of a Ballasted pH Indicator (DNSA Indicator-Polyvinyl Alcohol)

Polyvinyl alcohol (100 g, Molecular Weight 31,000–50,000, Aldrich Chemicals, Milwaukee, Wis.) was dissolved in deionized water (800 ml) by stirring at about 80° C. In a separate beaker, DNSA pH indicator [2-(2,4-dinitrophenylazo)-6-(N-methyl-N-(2-hydroxysulfonyl-oxy-ethylsulfonyl)amido)-1-naphthol-3-sulfonic acid] (2 g, 3.1 millimoles, E. Merck, Darmstadt, Germany, as described in U.S. Pat. No. 4,029,598) and $Na_2CO_3$ (32 g, 300 millimoles, J. T. Baker Company, Phillipsburg, N.J.) were dissolved in deionized water (150 ml) by stirring at room temperature. A 32% aqueous NaOH solution (20 ml) was added to the polyvinyl alcohol solution and mixed by stirring on a magnetic stir plate. The DNSA solution was then added in 2-ml aliquots, waiting between aliquots for complete mixing with the polyvinyl alcohol solution. The solution was stirred for 6 hours at room temperature. The resulting DNSA-polyvinyl alcohol was precipitated in 4 batches by adding 250 ml of the reaction mixture dropwise to 2 l of methanol while vigorously stirring with a propeller-style overhead stir blade. Pouring the mixture over an 80-mesh wire screen isolated the precipitated polymer. The precipitate was then washed with 3 washes of methanol (approximately 500 ml per wash) until no more blue color eluted. The methanol washes were followed by 3 washes of ether (approximately 500 ml per wash). The washed polymer was then air dried overnight in a large, uncovered foil pan.

The dried polymer was then dissolved in deionized water (800 ml) by stirring at about 80° C. and again precipitated, isolated, and washed as outlined above. The washed polymer was air dried overnight followed by drying under vacuum at room temperature. The mass of DNSA-polyvinyl alcohol ballasted pH indicator recovered was 80 g.

For comparison, a sample of DNSA-ethanol was prepared in exactly the same manner, except that the reaction was run in 50% (v/v) ethanol as solvent.

Example 2

Amount of DNSA Indicator Bound to the Polyvinyl Alcohol

The purpose of this example was to determine the amount of DNSA indicator bound to the DNSA-polyvinyl alcohol ballasted pH indicator prepared in Example 1.

The extinction coefficient of DNSA pH indicator in aqueous 0.1 M NaOH was determined spectrophotometrically to be 23,220 L/mol cm at a wavelength of maximum absorbance of 589 nanometers (nm).

This extinction coefficient was used to determine the amount of DNSA indicator in a 0.1 M NaOH solution of DNSA-polyvinyl alcohol. The visual spectra of free DNSA in solution and ballasted DNSA in solution are identical and thus the assumption was made that the extinction coefficient of bound DNSA is the same as DNSA in solution. By comparing the absorbance at 589 nm of a solution of ballasted DNSA to a solution of DNSA of known concentration, the amount of DNSA bound to the polyvinyl alcohol was determined to be approximately 5 mg of DNSA per g of polyvinyl alcohol. Thus, theoretically, for every 100 g of polyvinyl alcohol used in the above procedure, 500 mg of DNSA becomes bound to the polyvinyl alcohol.

Example 3

Preparation of Thin Film, Dry Culture Device Containing DNSA Indicator-Polyvinyl Alcohol The DNSA-polyvinyl alcohol ballasted pH indicator (6 g) prepared in Example 1 was dissolved in deionized water (100 ml) by stirring for 30 minutes at 80–90° C. The resulting dark blue solution was cooled to room temperature and nutrients and bile salts were then added to make an EB culture medium (EB culture medium is the same as Difco VRBA without an indicator dye and with 5% glucose used in place of lactose; see p.1053 of 1984 Difco Manual, Difco Labs, Detroit, Mich.). This mixture was then warmed to 50° C., and M150 guar gum (1 g, Rhone-Poulenc, Kreuzlinger, Switzerland) was added. The resulting warm viscous mixture was coated on 7-mil polyester substrate film (Imperial Chem. Industries, Wilmington, Del.) at a thickness of 20-mil and then dried for 20 minutes at about 143° C. A thin film culture device containing the DNSA-polyvinyl alcohol ballasted pH indicator was then constructed with a guar gum-coated polypropylene cover sheet and a Styrofoam spacer as described in Example 1 of U.S. Pat. No. 5,723,308. Comparative devices were prepared in the same manner, except that equivalent molar amounts of either DNSA indicator alone or DNSA-ethanol indicator (from Example 1) was substituted for the DNSA-polyvinyl alcohol ballasted pH indicator. The relative 0i:3 amounts of these indicators were determined by optical density measurements at a wavelength of 589 nm assuming the same extinction coefficient for DNSA indicator and its adducts as described in Example 2.

Example 4

Detection of Bacteria Growth

Both *E. Coli* 149 (ATCC 55535) and C1 (*Serratia liquifaciens*) were grown for 24 hours at 37° C. on the thin film culture devices described in Example 3 according to the procedure described in Example I of U.S. Pat. No. 5,723, 308. Measurements were made of the diameters of the resulting color zones and the results from the device containing DNSA-polyvinyl alcohol (PVA) ballasted pH indicator were compared with the results of the devices containing either free DNSA indicator or DNSA-ethanol indicator. The *E. coli* 149 and C1 bacteria species were chosen because they encompass the whole range of acid-producing bacteria from very low acid production (C1) to very high acid production (*E. coli* 149).

Results are shown in Table 1. These results show the differences in color zone diameter attributed to both pKa changes and to the changes in ballasting of the DNSA pH indicator. Thus, the color zone diameter was significantly reduced by changing from the free DNSA indicator (pKa= 7.6) device to the DNSA-ethanol (pKa=6.9) device. The color zone diameter was further significantly reduced by changing from the DNSA-ethanol (pKa=6.9) device to the DNSA-polyvinyl alcohol (pKa=6.9) device. The latter results clearly show the effect of reducing the color zone diameter by using a high molecular weight ballast such as polyvinyl alcohol versus using a low molecular weight compound such as ethanol. The results suggest that detecting color zones from growing bacteria can be aided by using a thin film culture device containing DNSA-polyvinyl alcohol, since the color zone diameters would be reduced and less likely to diffuse together during the incubation period.

TABLE 1

| | Color Zone Diameters (mm) on Thin Film Culture Devices Mean ± Standard Error (Number of Colonies) | | |
|---|---|---|---|
| Bacteria Species | Free DNSA (pKa = 7.6) | DNSA-Ethanol (pKa = 6.9) | DNSA-PVA (pKa = 6.9) |
| *E. coli* 149 | 8.0 ± 1.1 (10) | 6.9 ± 0.3 (10) | 3.49 ± 1.1 (16) |
| C1 | 6.1 ± 1.1 (13) | 5.3 ± 0.8 (13) | ≦1.0 |

Example 5

Preparation of Ballasted pH Indicators (Carboxy Phenol Red pH Indicator Bound to Amino-Modified Dextrans)

The following procedure was used to covalently bind carboxy phenol red pH indicator to amino-modified dextrans of varying molecular weight.

Amino-modified dextran (0.5 g, MW=10,000, Molecular Probes, Eugene, Oreg.) was suspended by stirring in dimethylformamide (DMF, 20 ml, Aldrich Chemical). Carboxy phenol red (CPR, Curtis Laboratories, Philadelphia Pa.) indicator (120 mg) was dissolved in DMF (20 ml) followed by the addition of coupling agents EDC [1-3-dimethylaminopropyl)-3-ethylcarbodiimide hydrochloride] (178 mg, Aldrich Chemical) and HOBt (1-hydroxy-benzotriazole hydrate) (81 mg, Aldrich Chemicals). The indicator/EDC/HOBt supernatant solution was then added to the dextran solution and the reaction mixture stirred for 3 days. The resulting slurry was then filtered on Whatman #4 filter paper using a Buchner funnel on a vacuum flask. The resulting cake was then dissolved in 4 ml of 10 mM sodium phosphate buffer (pH 8.0). Undissolved material was allowed to settle and the clear supernatant liquid was transferred to a dialysis bag with a molecular weight cut-off of 6–8000 Daltons. After dialysis against 4 l of distilled water for 24 hours (with 4 changes of water) the dialysis bags were placed on a glass dish and covered with solid Ficoll (MW=40,000, Sigma Chemical, St. Louis, Mo.) for 4–6 hours until the volume of the solution of dextran-CPR conjugate was reduced at least 50%. This solution was stored at 4° C. until used. A CPR-dextran (MW=40K) ballasted pH indicator was prepared as described above, except that the amino-modified dextran had a molecular weight of 40,000.

Example 6

Preparation of Thin Film Culture Device Containing CPR-Dextran Indicators

The amount of CPR chromaphore present in each of the CPR-Dextran ballasted pH indicators prepared as described in Example 5 was determined spectrophotometrically at a wavelength of 560 nm in a manner analogous to the method described in Example 2. Aqueous solutions of CPR-Dextran indicators were individually mixed with EB culture medium as described in Example 3 to give media containing 0.2 mg of CPR/ml. The resulting culture media were then used to prepare thin film culture devices as described in Example 3. A comparative device was prepared in the same manner, except that an equivalent molar amount of CPR indicator alone was substituted for the CPR-dextran (MW=10K or 40K) ballasted pH indicator.

Example 7

Detection of Bacteria Growth

Both *E. Coli* 149 (ATCC 55535) and C1 (*Serratia liquifaciens*) were grown for 24 hours at 37° C. on the thin film culture devices described in Example 6. Measurements were made of the diameters of the resulting color zones and the results from the devices containing the CPR-dextran ballasted pH indicators were compared with the results of the device containing the free CPR indicator. The color zone diameters were measured for as many colonies as possible on the device. Colonies growing very close to the edge of the foam dam or less than 2 mm away from another colony were not measured. A visual check on the ease with which distinct color zones could be counted was also noted.

Results are shown in Table 2. In the testing with the strong acid-producer *E. coli* 149, the results show a trend to smaller color zone diameter by ballasting the CPR pH indicator with amino-modified dextran and the data indicate that the effect of decreasing the zone diameter was greater for the dextran of higher molecular weight. In the testing with the weak-acid producer C1, the diameters of color zones were not significantly different. However, a visual observation was made that the bacteria colonies of the CPR-dextran (MW=40K) indicator device had sharper edges and were easier to read with respect to fused together zones than the bacteria colonies on the free CPR indicator device.

TABLE 2

| Bacteria Species | Color Zone Diameters (mm) on Thin Film Culture Devices Mean ± Standard Error (Number of Colonies) | | |
|---|---|---|---|
| | Free CPR | CPR-Dextran (MW = 10K) | CPR-Dextran (MW = 40K) |
| E. coli 149 | 5.4 ± 0.6 (42) | 5.1 ± 0.52 (72) | 4.42 ± 0.51 (52) |
| C1 | 4.0 ± 0.5 (57) | 3.8 ± 0.5 (43) | 3.8 ± 0.5 (38) |

All patents, patent documents, and publications cited in this document are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A culture medium for the detection and enumeration of microorganisms comprising a water-soluble ballasted pH indicator comprising a pH indicator bound to a hydrophilic substance.

2. The medium of claim 1 wherein the medium further comprises a cold water soluble powder.

3. The medium of claim 1 wherein said medium is coated on a waterproof substrate.

4. The medium of claim 1 wherein said pH indicator is selected from the group consisting of monoazo dyes; polyazo dyes; amino-, hydroxy-, and aminohydroxy- arylmethanes (di- and tri-arylmethanes); modified phenolphthaleins; modified sulfonphthaleins; anthroquinones; xanthenes; polycyclic aromatics; and naphthofluoresceins.

5. The medium of claim 1 wherein said pH indicator comprises 2-(2,4-dinitrophenylazo)-6-[N-methyl-N-(2-hydroxysulfonyl-oxy-ethylsulfonyl)amido]-1-naphthol-3-sulfonic acid.

6. (Amended) The medium of claim 1 wherein said pH indicator comprises carboxy phenol red.

7. The medium of claim 1 wherein said hydrophilic substance is selected from the group consisting of modified celluloses, polyvinyl alcohol, dextrans, amino-modified dextrans, modified guar gums, guar gums, xanthan gums, and locust bean gums.

8. The medium of claim 1 wherein said hydrophilic substance is polyvinyl alcohol.

9. The medium of claim 1 wherein said hydrophilic substance is an amino-modified dextran.

10. The medium of claim 1 wherein said pH indicator is a fluorescent indicator.

11. The medium of claim 1 wherein said pH indicator has a pKa value between about 6 and about 8.

12. The medium of claim 1 wherein said ballasted pH indicator is present at a concentration of about 0.25 mg/ml to about 1.0 mg/ml.

13. The medium of claim 1 wherein said medium further comprises at least one nutrient and one gelling agent.

14. A method of detecting and enumerating microorganisms in a sample, comprising:
   adding the sample to a culture medium comprising a water-soluble ballasted pH indicator comprising a pH indicator bound to a hydrophilic substance; and
   detecting the color or fluorescence change of the ballasted pH indicator in the medium.

15. The method of claim 14 wherein the sample is added to a device including a self-supporting waterproof substrate.

16. The method of claim 14 wherein said pH indicator is selected from the group consisting of monoazo dyes; polyazo dyes; amino-, hydroxy-, and aminohydroxy-arylmethanes (di- and tri-arylmethanes); modified phenolphthaleins; modified sulfonphthaleins; anthroquinones; xanthenes; polycyclic aromatics; and naphthofluoresceins.

17. The method of claim 14 wherein said pH indicator comprises 2-(2,4-dinitrophenylazo)-6-[N-methyl-N-(2-hydroxysulfonyl-oxy-ethylsulfonyl)amido]-1-naphthol-3-sulfonic acid.

18. The method of claim 14 wherein said pH indicator comprises carboxy phenol red.

19. The method of claim 14 wherein said hydrophilic substance is selected from the group consisting of modified celluloses, polyvinyl alcohol, dextrans, amino-modified dextrans, modified guar gums, guar gums, xanthan gums, and locust bean gums.

20. The method of claim 14 wherein said hydrophilic substance is polyvinyl alcohol.

21. The method of claim 14 wherein said hydrophilic substance is an amino-modified dextran.

22. A culture medium device, comprising:
   (a) a substrate; and
   (b) a medium for growing microorganism comprising a water-soluble ballasted pH indicator comprising a pH indicator bound to a hydrophilic substance, wherein the medium is disposed on the substrate.

23. The device of claim 22 further comprising a water-based adhesive disposed between the substrate and the medium.

24. The device of claim 22 further comprising a cover sheet disposed over the medium.

25. The device of claim 24 wherein said cover sheet is transparent.

26. The device of claim 22 wherein said pH indicator is selected from the group consisting of monoazo dyes; polyazo dyes; amino-, hydroxy-, and aminohydroxy- arylmethanes (di- and tri-arylmethanes); modified phenolphthaleins; modified sulfonphthaleins; anthroquinones; xanthenes; polycyclic aromatics; and naphthofluoresceins.

27. The device of claim 22 wherein said pH indicator comprises 2-(2,4-dinitrophenylazo)-6[N-methyl-N-(2-hydroxysulfonyl-oxy-ethylsulfonyl)amido]1-naphthol-3-sulfonic acid.

28. The device of claim 22 wherein said pH indicator comprises carboxy phenol red.

29. The device of claim 22 wherein said hydrophilic substance is selected from the group consisting of modified celluloses, polyvinyl alcohol, dextrans, amino-modified dextrans, modified guar gums, guar gums, xanthan gums, and locust bean gums.

30. The device of claim 22 wherein said hydrophilic substance is polyvinyl alcohol.

31. The device of claim 22 wherein said hydrophilic substance is an amino-modified dextran.

* * * * *

UNITED STATES PATENT AND TRADEMARK OFFICE
CERTIFICATE OF CORRECTION

PATENT NO. : 6,391,626 B1  Page 1 of 1
DATED : May 21, 2002
INVENTOR(S) : Adams, Carl A.

It is certified that error appears in the above-identified patent and that said Letters Patent is hereby corrected as shown below:

Column 4,
Line 56, "4,565,783" should read -- 4,565,383 --.

Column 7,
Line 23, "Example I" should read -- Example 1 --.

Column 9,
Line 39, delete "(Amended)".

Column 10,
Line 18, "O;:3" should be deleted.
Line 28, "microorganism" should read -- microorganisms --.

Signed and Sealed this

Twenty-eighth Day of January, 2003

JAMES E. ROGAN
*Director of the United States Patent and Trademark Office*